United States Patent

Salo et al.

[19]

[11] Patent Number: 6,058,329
[45] Date of Patent: May 2, 2000

[54] OPTIMIZATION OF PACING PARAMETERS BASED ON MEASUREMENT OF ACOUSTIC NOISE

[75] Inventors: Rodney W. Salo, Fridley; Kevin G. Nugent, Minneapolis, both of Minn.

[73] Assignee: Cardiac Pacemakers, Inc., St. Paul, Minn.

[21] Appl. No.: 09/306,858

[22] Filed: May 7, 1999

Related U.S. Application Data

[62] Division of application No. 09/170,259, Oct. 13, 1998.

[51] Int. Cl.⁷ .................................................. A61N 1/365
[52] U.S. Cl. ........................................................ 607/17
[58] Field of Search ................................ 607/17, 18, 19, 607/27

[56] References Cited

U.S. PATENT DOCUMENTS 5,540,727  7/1996  Tockman et al. .......................... 607/17
5,700,283  12/1997  Salo .......................................... 607/18

*Primary Examiner*—William E. Kamm
*Assistant Examiner*—George R. Evanisko
*Attorney, Agent, or Firm*—Nikolaim Merserea & Dietz, P.A.

[57] ABSTRACT

Hemodynamic performance of the heart as a pump is optimized by using an accelerometer and signal processing circuitry to measure total acoustic noise (TAN) over predetermined time periods when a pacemaker is made to function in a variety of modes. By detecting the particular mode associated with minimum TAN, the optimum pacing mode is arrived at.

4 Claims, 5 Drawing Sheets

OPTIMIZATION OF PACING PARAMETERS BASED ON MEASUREMENT OF ACOUSTIC NOISE

This is a Divisional of copending application Ser. No. 09/170,259, filed on Oct. 13, 1998.

BACKGROUND OF THE INVENTION

I. Field of the Invention

This invention relates generally to cardiac rhythm management in the treatment of patients exhibiting congestive heart failure (CHF), and more particularly to an apparatus and method for measuring total acoustic noise (TAN) during each heart beat or acoustic noise measured in predetermined defined segments of a cardiac cycle and utilizing the measured value to optimize the pacing mode for a given CHF patient.

II. Discussion of the Prior Art

Early on in the development of so-called rate-adaptive pacemakers in the treatment of bradycardia it has been recognized that an accelerometer can be incorporated into the implantable pacemaker device for sensing physical activity so that the pacing rate can automatically be adjusted between upper and lower limits to accommodate the patient's hemodynamic demand. That is to say, an activity sensor in the form of a piezoresistive bridge can be used to produce an electrical control signal that varies with the level of physical activity of the patient. More recently, cardiac stimulating systems have been designed for implantation in patients suffering from CHF and various algorithms have been devised for optimizing the mechanical performance of the heart as a pump by appropriately adjusting the AV delay parameter of the pacemaker. In this regard, reference is made to the Lawrence C. Baumann, et al. application Ser. No. 08/815,697, filed Mar. 12, 1997, now U.S. Pat. No. 5,836,787 and entitled ※Apparatus and Method for Optimizing the Cardiac Performance by Determining the Optimal Timing Interval from an Accelerometer Signals※ as well as the V. A. Kadhiresan application Ser. No. 09/009,424, filed Jan. 20, 1998 now U.S. Pat. No. 5,935,081 and entitled ※Long Term Monitoring of Acceleration Signals for Optimization of Pacing Therapy※, both of which are assigned to applicant's assignee and their contents incorporated by reference herein.

Studies conducted by applicant's assignee, in which accelerometer signals from CHF patients were collected and analyzed, confirm that the heart generates acoustic energy (sound) as a by-product of its normal function. The character of this energy, in terms of its frequency spectrum, amplitude, morphology, etc., is determined by preload, after-load, contractility and cardiac chamber timing and, thus, is affected by factors, such as the atrio-ventricular (AV) interval and pacing site(s) (right chamber, left chamber or both chambers or multiple sites in any chamber). The analysis of accelerometer signals from CHF patients has revealed that the accelerometer signals increased in amplitude during exercise and increased linearly with patient workload, and that under fixed conditions, the overall accelerometer amplitude decreases as the pacing parameters approach optimum values, as defined by aortic pulse pressure or the peak positive rate of change of left ventricular pulse pressure with respect to time (LVdP/dt). LVdP/dt is a known measure of the heart's contractility. Upon noting the above relationships in data sampled from a number of CHF patients, we defined a parameter TAN, an acronym for Total Acoustic Noise, as the high pass filtered and rectified accelerometer signal integrated over a cardiac cycle for each heart beat. TAN values were derived by high pass filtering the raw accelerometer output signal with a filter having a corner frequency of about 1.0 Hz to remove baseline variations due primarily to respiration. Next, the high pass filtered accelerometer signal was rectified to produce a monopolar signal and that signal was integrated over each cardiac cycle.

The use of the TAN measure was first envisioned as a rate-adjusting parameter in a rate-adaptive pacemaker. It was noted that the amplitude of the accelerometer signal increases with exercise and is monotomically related to work load as well as to peak aortic blood velocity. Based on those relationships. It was originally thought that during a pacing optimization protocol that TAN would be maximized at the optimum pacing site and AV interval. This would seem reasonable in that it would coincide with the maximum cardiac output or pulse pressure. Instead, we found that aortic pulse pressure was a maximum when TAN was a minimum. In the same way that optimum tuning of an automobile engine results in minimum generated noise, so too does optimum AV interval result in a minimum TAN value at any given work load.

The Kieval U.S. Pat. No. 5,554,177 teaches that in cardiomyopathy, there is a particular abnormal heart sound which is minimized during an optimization process. Using the automobile engine analogy, this would be the equivalent of detecting an engine ※knock※ and then adjusting the timing to reduce its amplitude. The method of the present invention relies upon TAN and is predicated on the fact that all of the acoustic energy generated by the heart during its entire cycle is artifact and that optimization of AV timing reduces the overall level of ※noise※. The approach of the present invention has the advantage of greater simplicity over the system described in the Kieval '177 patent. It does not require that a particular objectionable acoustic component be identified, but instead, all of the acoustic signal generated by the heart can be integrated and the pacing mode modified so as to minimize the total acoustic noise. The TAN approach of the present invention is simpler and easier to implement. Since it is not necessary to identify S1 and S2 heart sounds, the processing power required is significantly reduced.

FIG. 1 is a plot of percentage change in TAN versus percentage change in LVdP/dt and FIG. 2 is a similar plot of aortic pulse pressure, each for both a left ventricular pacing site and for biventricular pacing sites measured during a pacing optimization protocol. These plots show that LVdP/dt (contractility) and pulse pressure maxima occur at the minimum TAN value, but also there is a linear negative relationship between the parameters. Our studies allow the conclusion to be drawn that the pacing site (LV pace or BiV pace) and the AV interval which will generate the maximum peak positive LVdP/dt and maximum aortic pulse pressure can be determined from the minimum TAN value.

Based upon the discovery that TAN is a minimum when an optimization protocol maximizes aortic pulse pressure and the heart's contractility, as evidenced by left ventricular dP/dt, a new algorithm has been developed for optimizing the hemodynamic performance of the heart in CHF patients.

SUMMARY OF THE INVENTION

The present invention provides a method and apparatus for optimizing the pacing mode of a cardiac pacemaker for patients having CHF. The apparatus comprises an implantable cardiac pacemaker having a plurality of programmable parameters for producing cardiac stimulating pulses at timed intervals, along with a means for applying the pulses to cardiac tissue at at least one site on or in the heart. Means are provided for measuring total acoustic noise (TAN) during successive cardiac cycles and for determining a minimum TAN measurement as the pacing parameters are varied. The pacing mode of the pacemaker is then set to the parameters associated with the minimum TAN measurements.

The means for measuring TAN comprise an accelerometer for sensing acoustic energy emitted from the heart and for producing a raw signal proportional to it. The raw signal is applied to a filtering circuit to attenuate variations in the raw signal due to respiratory activity and the filtered signal is then full-wave rectified to produce a monopolar output. The monopolar output from the rectifying device is then integrated over the period of each cardiac cycle.

The method of optimizing the pacing mode of the pacemaker includes the steps of providing a cardiac pacemaker having a plurality of programmable parameters where the pacemaker is coupled to a patient's heart for delivering pacing pulses to it in accordance with selected programmable parameters. The total acoustic noise is measured on a beat-by-beat basis while the patient is at rest and while pacing the patient's heart over a range of values for each of the plurality of programmable parameters. The measured results are stored for later comparison to determine which of the plurality of parameters is associated with minimum TAN values. The pacemaker is then programmed to the parameter values associated with the minimum TAN values.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which.

DESCRIPTION OF THE PREFERRED EMBODIMENTS

Figure 1:
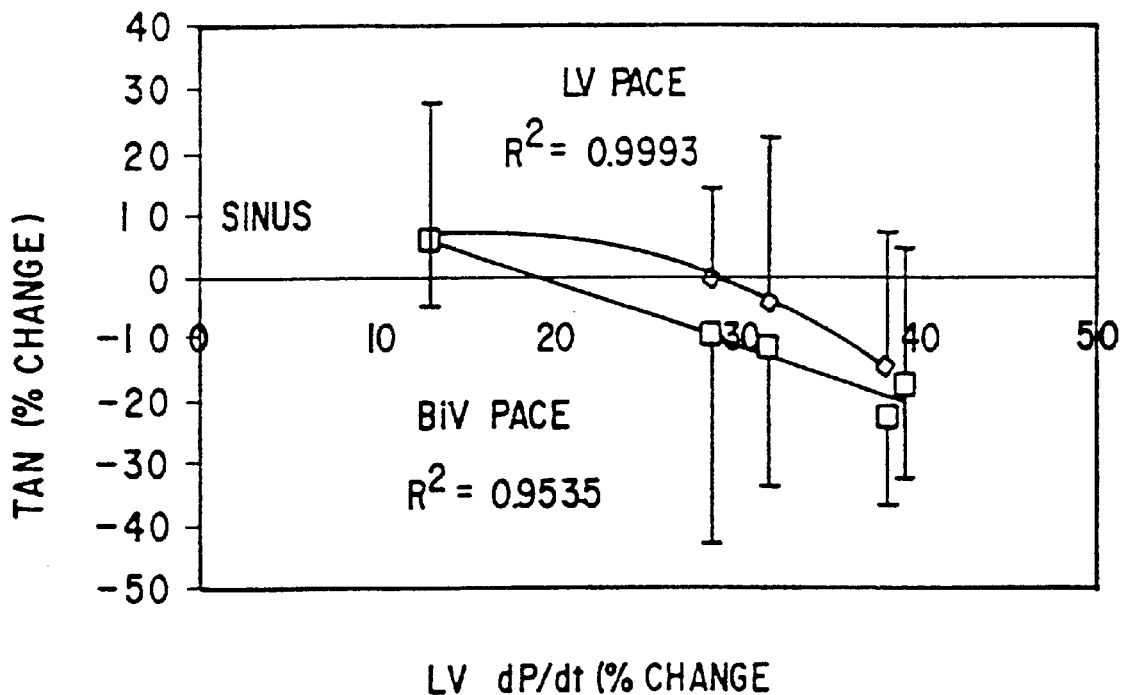
FIG. 1 is a plot of total acoustic noise vs. peak positive left ventricular dP/dt for biventricular pacing and for left ventricular pacing.
Figure 2:
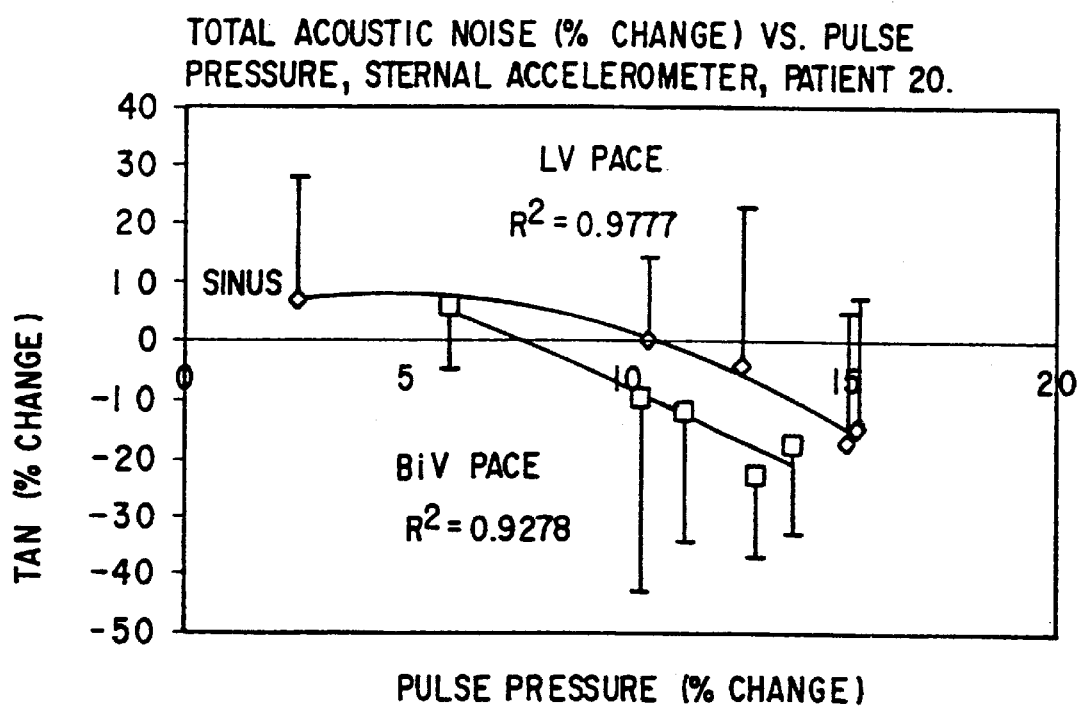
FIG. 2 is a plot of aortic pulse pressure vs. total acoustic noise for either left ventricular or biventricular pacing.
Figure 3:
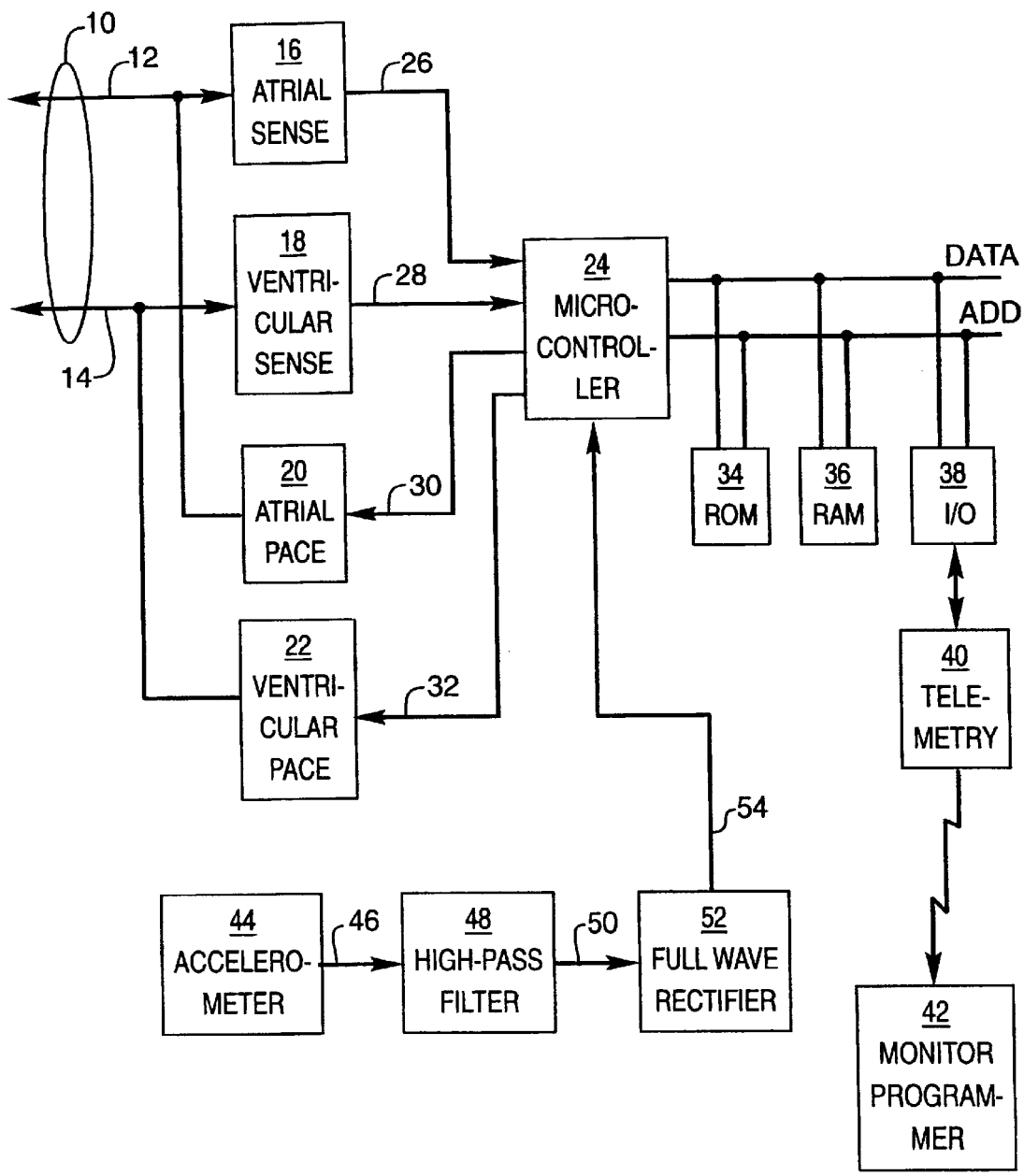
FIG. 3 is a schematic circuit diagram of an implantable cardiac stimulating device incorporating the optimization circuitry in accordance with the present invention.

Referring to FIG. 3, there is illustrated by means of a block diagram apparatus for implementing the present invention in an implantable cardiac stimulating device such as a dual chamber bradycardia pacemaker. It includes pacing leads 10 having electrodes (not shown) for placement on endocardial or myocardial tissue and insulated conductors 12 and 14 used to convey electrical signals to and from the electrodes. The conductor 12 will typically lead to an electrode positioned to sense and stimulate the atrial chamber while conductor 14 conveys electrical signals to and from one or more electrodes positioned to stimulate the right ventricle or the left ventricle or both the right and left ventricles in the case of the biventricular pacing.

Included in the implantable pacemaker is an atrial sense amplifier 16, a ventricular sense amplifier 18, an atrial stimulating pulse generator 20 and a ventricular pacing pulse generator 22. As is well known in the art, the atrial sense amplifier circuitry 16 detects atrial depolarization events (P-waves) while the ventricular sense circuit 18 detects ventricular depolarization events (R-waves). The outputs from the atrial sense amplifier and the ventricular sense amplifier are applied to a microprocessor-based controller or microcontroller 24 via conductors 26 and 28, respectively. The microcontroller 24 responds to the inputs and issues appropriate control signals over lines 30 and 32 to cause the atrial pulse generator 20 and the ventricular pulse generator 22 to issue cardiac stimulating pulses at times determined by software programmed into the microcontrollers ROM memory 34. Alterable operating parameters are typically stored in a RAM memory 36. For example, RAM 36 may store information determining stimulating pulse amplitude, stimulating pulse width, stimulating rate and the atrialventricular delay (AV delay) that establishes a time interval between the occurrence of a given P-wave and the time that a stimulating pulse will be issued.

Also connected to the data and address buses to which the ROM 34 and RAM 36 are coupled is an IO interface 38. A conventional telemetry circuit 40 allows communication of data between the implanted pacemaker and an external monitor/programmer 42. It is through this telemetry link that the cardiologist may enter new pacing parameters into the RAM memory 36 and to receive data for analysis to assess the efficacy of the particular pacing protocol then being carried out by the software.

In implementing the optimization scheme of the present invention, the implantable device further includes an accelerometer 44 located within the moisture impervious, hermetically sealed housing or can of the pacemaker containing the electronic circuitry depicted. The pacemaker housing may be implanted at various locations relative to the heart so as to accentuate the vibratory force components reaching and sensed by the accelerometer 44. The accelerometer 44 produces a raw accelerometer signal on line 46 that includes heart sounds, components due to chest wall movement due to respiratory activity and components due to other internal and external sources of acoustic energy. The output from the accelerometer is operated on by a high pass filter 48 having a corner frequency of about 1 Hz which is effective to attenuate lower frequency components, such as those due to such respiratory activity. The output from the high pass filter on line 50 is then full-wave rectified by rectifier circuit 52 which effectively reduces the bipolar input signal to a monopolar output signal. The output from the full wave rectifier is then applied as an input to the microcontroller 24.

Contained within the microcontroller 24 is an analog-to-digital converter (not shown) which converts the monopolar waveform on its input line 54 to a digital quantity. Those skilled in the art can appreciate that it would be possible to feed the raw accelerometer signal 46 directly into the microcontroller 24 where that raw signal would be digitized and then the high-pass filtering and full wave rectification of that digitized raw signal can be carried out in the digital domain rather than in the analog domain.

The microcontroller 24 is programmed to integrate the digitized full-wave rectified and filtered accelerometer signal on a beat-by-beat basis. For this purpose, either a P-wave input on line 26 or a R-wave input on line 28 may be used to gate the integrator output so that the area under the full-wave rectified and filtered accelerometer signal curve will be sampled and stored in the RAM memory 36 as the TAN. As an optional step, the TAN value obtained via the integration step may be normalized by dividing it by the product of the sampling rate of the integrator and the cardiac cycle length.

Before describing in greater detail the manner in which the pacing parameters are optimized, it is felt expedient to first describe how the same optimization protocol can be carried out with an external, non-implanted system. In this regard, reference is made to the schematic diagram of FIG. 4.

Figure 4:
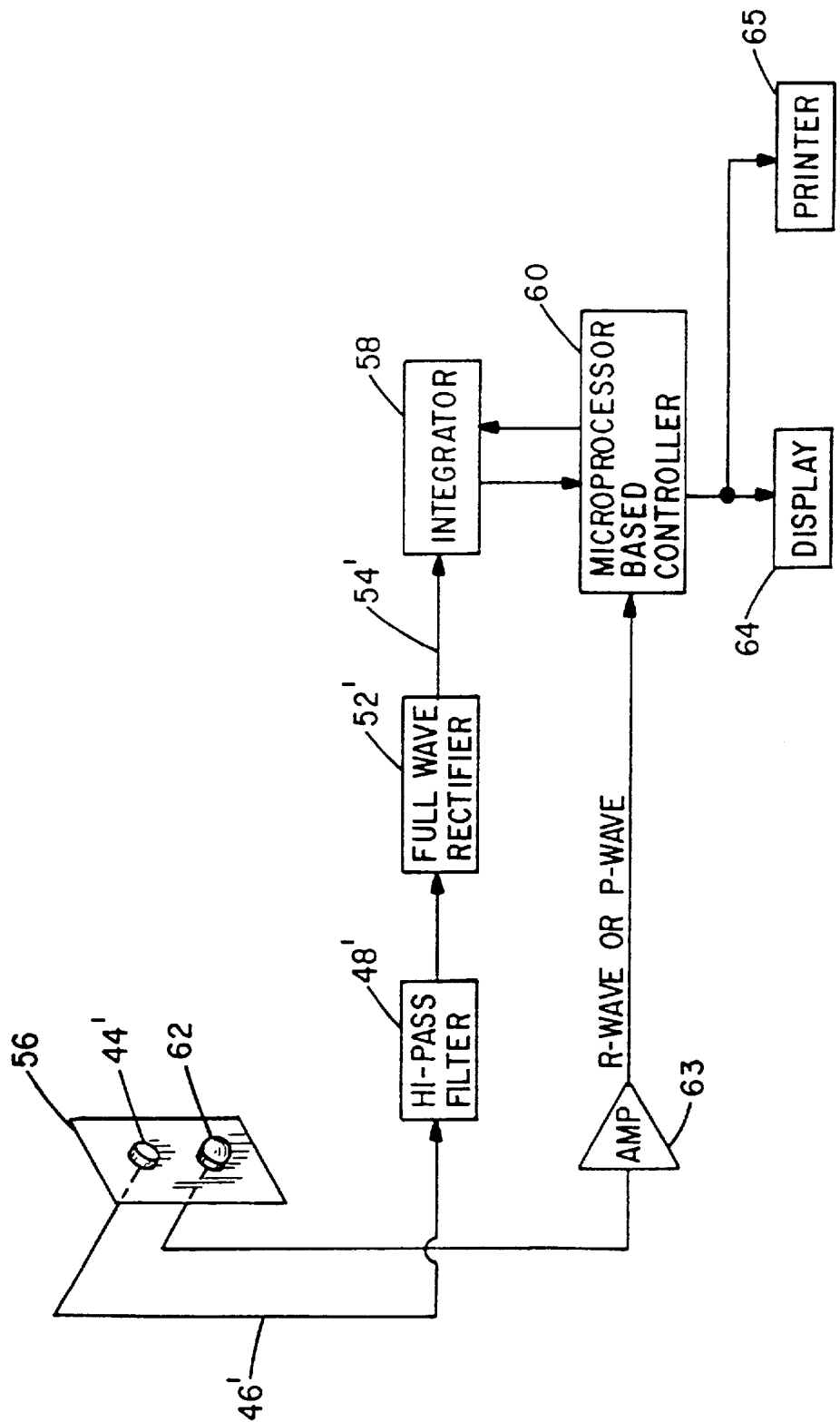
FIG. 4 is a schematic block diagram of the circuitry implementing the present invention in an external apparatus.

In the external unit, a piezoresistive bridge accelerometer 44' is shown as being affixed to a band 56 adapted to be worn about the patient's chest so that the accelerometer 44' will be located at a preferred location on the chest wall such as the pectoral region or proximate the apical portion of the heart. As with the embodiment of FIG. 3, the raw accelerometer signal on line 46' is applied to a high pass filter 48' and then to a full-wave rectifier 52', with the resulting signal on line 54' being applied to an integrator 58. The sampling rate of the integrator is controlled by a microprocessor-based controller 60. Also affixed to the band 56 is an ECG electrode 62 capable of detecting cardiac depolarization events, both R-wave and P-wave. These signals are shaped and amplified in amplifier 63 and either the R-wave signal or the P-wave signal may be used to define the period over which the waveform on input line 54' to the integrator 58 is integrated. In accordance with the present invention, integration occurs on a beat-by-beat basis. Again, while the integrator 58 is illustrated in FIG. 4 as being a separate component, the integration function can be performed in the digital domain within the microprocessor-based controller as can all of the signal processing represented by the filter 48' and the full-wave rectifier 52'. It will be recognized that the cardiac cycle can also be defined by R-wave events or P-wave events derived by and telemetered from the implanted pacer rather than from a surface electrode, such as electrode 62 in FIG. 4.

The integrated value of the acoustical signal during a single heart beat cycle (from P-wave to P-wave or from R-wave to R-wave) is referred to as the total acoustic noise (TAN).

The patient on whom the band 56 is applied will also typically have a pacemaker implanted, with the pacemaker being of the type permitting its parameters to be reprogrammed from an externally applied pacemaker programmer of a conventional, commercially-available type. As such, the attending medical professional may program a particular operating mode into the implanted pacemaker and then use the apparatus of FIG. 4 to monitor any changes in TAN detected following the mode change. The information can be visually displayed at a terminal 64 and/or provided in hard copy via a printer/plotter 65.

In either of the embodiments of FIGS. 3 and 4, if it is found that measurements need be taken in an environment in which there is a relatively high level of ambient acoustic noise, it may be expedient to ensemble average the raw accelerometer data over a plurality of beats. Again, this can be done in the digital domain and information defining the start of each cardiac cycle is readily available from cardiac depolarization events, either P-wave or R-wave. It is also preferable that the patient be at rest to further minimize non-cardiac related noise picked up by the accelerometer. The fact that the patient is at rest may be inferred from the accelerometer by an average TAN value less than a predetermined activity threshold.

Instead of the single-axis accelerometer as in the embodiments shown in FIGS. 3 or 4, a multiple axis (2 or 3) accelerometer may be used to monitor TAN as a multidimensional quantity. For example, a three-dimensional accelerometer may be constructed from three single axis accelerometers oriented along three orthogonal axes. In such an embodiment, the acceleration measured by the three accelerometers would correspond to three components of an acoustic vector. TAN may be computed from any property of this vector. For example, TAN could be $$\sqrt{ACC_x^2 + ACC_y^2 + ACC_z^2}$$

computed from the magnitude of the vector magnitude
where $ACC_x$=x component of acceleration measured by
accelerometer oriented in ▒x▒ direction
where $ACC_y$=y component of acceleration measured by
accelerometer oriented in ▒y▒ direction
where $ACC_z$=z component of acceleration measured by
accelerometer oriented in ▒z▒ direction.

Figure 5:
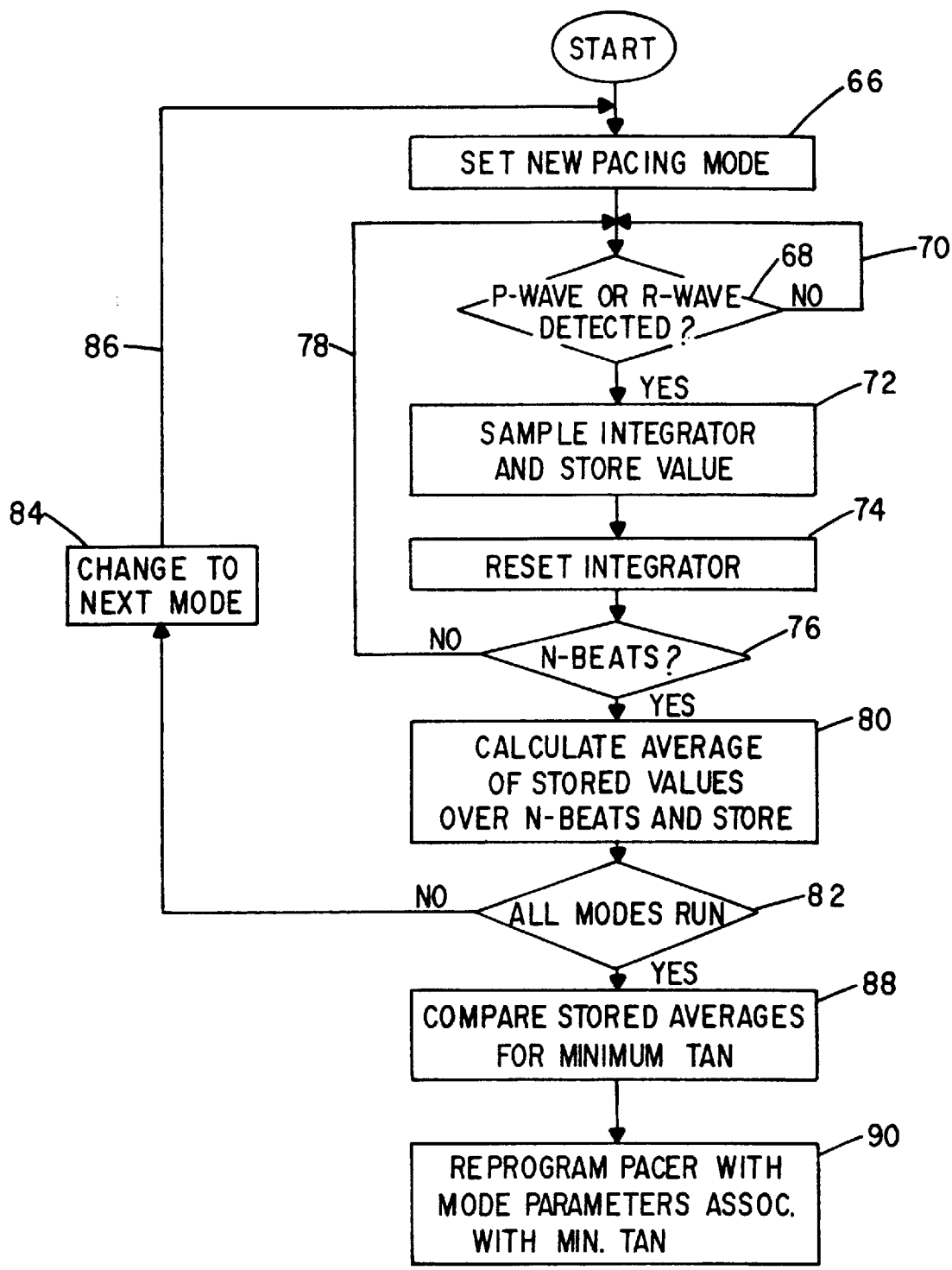
FIG. 5 is a software flow diagram illustrating the algorithm executed by the microcontroller of FIG. 3 and the microprocessor-based controller of FIG. 4.

Turning now to FIG. 5, there is shown a software block diagram of the algorithm carried out in the microcontroller 24 of the embodiment of FIG. 3 or in the microprocessor-based controller 60 in the embodiment of FIG. 4. Upon start-up, the first operation is for the attending physician to set a new pacing mode into the implanted pacemaker (block 66). A mode change may involve a change in pacing pulse frequency, the length of the AV delay, the chamber or chambers being paced, the location(s) within a given chamber where the pacing electrode(s) are placed, etc. A test may be made to determine whether the patient is at rest by applying a bandpass filter to the accelerometer signal with corner frequencies at 1 Hz and 10 Hz to extract the body motion related components. The TAN may then be computed from the filtered signal and then averaged over several beats (5–100) to obtain the average body activity. If this average is less than a predetermined threshold, the patient is considered to be at rest. Preferably, with the patient at rest to further minimize noise due to body motion, a test is then made at decision block 68 as to whether a selected one of either P-waves or R-waves is being sensed and, if not, control loops back over path 70 and sampling continues until the selected one of either P-waves or R-waves is detected. At that point, the output of the integrator is sampled and stored in a RAM memory 36 (FIG. 3). It is further to be understood that the microprocessor-based controller 60 in FIG. 4 would also include a ROM and a RAM. Once the integrator is sampled, it is reset (block 74). Next, a test is made at decision block 76 to determine whether a predetermined number of beats, N, have had their TAN value sampled and stored and, if not, control loops back over line 78 to the input of decision block 68 and the intervening steps 68, 72 and 74 are repeated until such time as N beats have occurred. At this point, the microcontroller computes the average of the stored TAN values over the N beats and then the average value is stored (block 80).

Next, at decision block 82, a decision is made as to whether all of the predetermined modes have been run. If not, a change is made to the next mode (block 84) and then control loops back over path 86 to the input of operation block 66. Once all of the modes have been run, the stored TAN averages are compared to determine which pacing mode was associated with the minimum TAN value. As has been indicated in the introductory portion of the present specification, tests on several patients has shown that the heart's contractility, as measured by LVdT/dt, and aortic pulse pressure are a maximum when TAN is a minimum and, hence, by reprogramming the implantable pacemaker with the mode parameters associated with minimum TAN (block 90) optimal hemodynamic performance in patients being treated for congestive heart failure is attained.

We have found that appreciably larger changes in TAN occur if a series of transient responses is created. For example, if TAN is monitored while in sinus rhythm and then pacing is allowed to take place in a particular mode and for a particular AV delay for only a small number of beats, for example, five to ten beats, the resultant paced TAN appears to be more sensitive to the pacing parameters than it is if measurements are made only during steady state pacing, i.e., pacing in each mode and at each AV delay for, say, two to three minutes before switching to the next mode. For further information on such a pacing protocol, reference is made to U.S. Pat. No. 5,487,752.

As a further alternative, rather than measuring acoustic noise over an entire cardiac cycle, i.e., TAN, it has been found that by computing the ratio of the integrated acoustic noise during ejection to the integrated acoustic noise during filling we can generate another parameter that may be used in an optimization algorithm. This ratio is used for optimization of cardiac function by searching for the maximum value measured as the pacing parameters are varied. The time of ejection and filling for determining the periods of integration can be determined from a non-invasive arterial pressure signal, from aortic flow via Doppler or from an accelerometer signal itself. If timing is extracted from the accelerometer signal, the ejection period would be the time from the beginning of heart sound S1 to the heart sound S2. The filling interval would then be from the time of occurrence of heart sound S2 to the occurrence of the next R-wave on the electrogram. For a teaching of how heart sound S2 can be derived from an implanted accelerometer signal, reference is made to copending application 08/766,339 filed Dec. 16, 1996 (now U.S. Pat. No. 5,792,195, issued Aug. 11, 1998). This ratio may then be used in an algorithm like that shown in FIG. 5 hereof in place of the TAN parameter.

It is further contemplated that the integrated acoustic noise during the filling phase of a cardiac cycle or during the ejection phase may be minimized or maximized in optimizing the pacer's AV delay parameter or the pacing site on the heart.

While the present invention has been described primarily as a way of optimizing the pacing mode of a cardiac pacemaker for patients having CHF, the high-pass filtered and rectified signal output from the accelerometer, when integrated over a cardiac cycle on a beat-by-beat basis can be used as a rate-adjusting parameter in a dual chamber pacemaker. In that TAN is found to increase with body activity, the TAN signal derived from heart sounds can be used in the same way as the output from an activity sensor in controlling the pacing rate of an implanted cardiac rhythm management device. To enhance such an arrangement, the raw (or high pass filtered) signal from the accelerometer would be ensemble averaged over a predetermined number of beats so to remove uncorrelated body motion artifacts. The pacing rate may then be set using a linear equation:

Pacing Rate=$m$ (TAN)+$b$ where $b$ is a base rate and $m$ is a slope parameter.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A method of optimizing a pacing mode of a cardiac pacemaker or a pacemaker/defibrillator for a patient, comprising the steps of:

(a) providing a cardiac pacemaker or pacemaker/defibrillator having a plurality of programmable parameters, said pacemaker or pacemaker/defibrillator being coupled to a patient's heart for delivering pacing pulses thereto in accordance with selected programmable parameters, (b) measuring total acoustic noise (TAN) on a beat-by-beat basis while pacing the patient's heart over a range of values for each of the plurality of parameters;

(c) storing the TAN values measured in step (b) and the values of each of the plurality of parameters with which the TAN value is associated;

(d) determining from the stored TAN values which of the plurality of parameters are associated with the minimum TAN values; and (e) programming the pacemaker or pacemaker/defibrillator with the parameters determined in step (d).

2. The method of claim 1 wherein the step of measuring total acoustic noise includes the further steps of:

(f) providing an accelerometer positioned on the patient at a site to sense movements due to cardiac activity and producing a raw electrical output signal proportional to such movement;

(g) filtering the raw electrical output signal to attenuate noise due to non-cardiac related movements;

(h) full-wave rectifying the filtered raw electrical output signal; and (i) integrating the rectified and filtered electrical output signal over each cardiac cycle.

3. The method as in claim 2 and further including the step of:

(j) ensemble averaging said raw electrical output signal prior to step (g).

4. The method as in claim 1 including the step of calculating an average TAN value from the measured beat-by beat TAN, comparing the calculated average TAN value to a predetermined activity threshold average TAN value to determine if the patient is at rest, storing the measured beat-by-beat TAN values measured in step (b) and the associated values of each of the plurality of parameters for those beats when the average TAN value is less than the threshold average TAN value indicating that the patient was at rest during the beat.

* * * * *